United States Patent
Davis et al.

(10) Patent No.: US 6,328,878 B1
(45) Date of Patent: Dec. 11, 2001

(54) ADHESIVE TAPE SENSOR FOR DETECTING AND EVALUATING COATING AND SUBSTRATE DEGRADATION UTILIZING ELECTROCHEMICAL PROCESSES

(75) Inventors: Guy D. Davis, Baltimore; Chester M. Dacres, Columbia; Lorrie A. Krebs, Baltimore, all of MD (US)

(73) Assignee: Dacco Sci, Inc., Columbia, MD (US)

( * ) Notice: Subject to any disclaimer, the term of this patent is extended or adjusted under 35 U.S.C. 154(b) by 0 days.

(21) Appl. No.: 09/372,074

(22) Filed: Aug. 11, 1999

(51) Int. Cl.$^7$ .............................. G01N 17/04; G01R 27/02
(52) U.S. Cl. ..................................... 205/776.5; 205/791.5; 324/71.2; 324/693; 324/700; 204/404
(58) Field of Search .................................... 324/693, 700, 324/707, 713, 722, 71.2; 205/776.5, 777, 791.5; 204/404; 422/53

(56) References Cited

U.S. PATENT DOCUMENTS

| | | | |
|---|---|---|---|
| 4,806,849 | * | 2/1989 | Kihara et al. .......................... 204/404 |
| 4,890,622 | * | 1/1990 | Ferrari ................................... 128/640 |
| 4,899,754 | * | 2/1990 | Bly et al. ............................... 128/640 |
| 5,069,774 | * | 12/1991 | Hladky et al. ......................... 204/404 |
| 5,306,414 | * | 4/1994 | Glass et al. ............................ 204/404 |
| 5,438,988 | * | 8/1995 | Duan et al. ............................ 128/640 |
| 5,859,537 | * | 1/1999 | Davis et al. ........................... 324/693 |
| 6,054,038 | * | 4/2000 | Davis et al. ....................... 205/776.5 |

OTHER PUBLICATIONS

Simpson et al "Evaluation of the effects of acidic deposition on coated steel substrates", Prog. Org. Coatings, 20 pp. 199–216, month unavail. 1992.*

* cited by examiner

Primary Examiner—Robert J. Warden, Sr.
Assistant Examiner—Kaj K. Olsen

(57) ABSTRACT

A portable and nondestructive adhesive tape corrosion sensor which is utilized under actual field or laboratory conditions in detecting coating and substrate degradation using Electrochemical Impedance Spectroscopy (EIS) of coated or uncoated metal structures has been developed. The invention allows for broad applicability, flexibility in utilizing the sensor in various environments without structural compromise and the ability to inspect and evaluate corrosion of the actual structure, regardless of the size, shape, composition, or orientation of the structure. The electrodes may be removed once a measurement is made or remain in the original fixed position so that subsequent measurements may be made with the same electrode. The nondestructive sensor apparatus is comprised of a pressure-sensitive adhesive tape that consists of a conductive film or foil and conductive adhesive overlapping another pressure-sensitive adhesive tape that consists of a conductive film or foil and non-conductive adhesive. The conductive tape serves as the sensing element or device. The non-conductive tape serves as the lead between the sensing element and the point of measurement. In an alternative configuration, the tape with the conductive adhesive may be used alone, acting as both sensor electrodes and the lead to the point of measurement. The metal structure or other substrate being sensed or evaluated for degradation serves as the working electrode. This two electrode sensing device is responsive to water uptake, incubation, and corrosion by measuring differences in impedance spectra. The invention can readily detect, quantify and monitor coating and metal degradation from its earliest stages, well before any visual indication of corrosion appears, under both laboratory and field conditions.

2 Claims, 2 Drawing Sheets

ADHESIVE TAPE SENSOR FOR DETECTING AND EVALUATING COATING AND SUBSTRATE DEGRADATION UTILIZING ELECTROCHEMICAL PROCESSES

BACKGROUND OF THE INVENTION

1. Field of the Invention

The present invention relates to a nondestructive and portable adhesive tape for detecting the various stages of metal and coating degradation by electrochemical corrosion. More specifically, the present invention relates to a portable electrochemical sensor which is utilized under field or actual environmental conditions for detecting coating and material or substrate degradation by electrochemical corrosion of both small and large coated or painted structures, as well as uncoated metal structures, thereby permitting detection of substrate degradation and electrochemical corrosion well before serious deterioration of the substrate or structure has occurred. The present invention is comprised of a conductive foil tape with a conductive, pressure-sensitive adhesive and another conductive foil tape comprises a non-conductive, pressure-sensitive adhesive. The conductive tape serves as the sensing element or device. The non-conductive tape serves as the lead between the sensing element and the point of measurement. Alternatively, the first tape can serve as both the sensing element and the lead. Used concurrently with one another through overlapping of the tapes in order to make electrical contact, both foil tapes serve as a detection sensor of substrate or coating degradation. Utilizing either configuration of the tapes, the sensor can be attached to a substrate of arbitrary shape, composition or orientation with the substrate serving as an electrochemical medium for physical and chemical analysis by exposure to selected external agents, physical or chemical, causing electrochemical alterations in the substrate's material, and changes in the chemical properties of the materials are then sensed and monitored for changes in the electrochemical impedance spectroscopy (EIS) spectra to read out the recorded information in correlation with the analyzed phenomenon or process for storage, monitoring or control purposes.

2. Prior Art

A major goal in the electrochemical field has long been to create a sensor which could be utilized in field or service conditions to detect corrosion and adhesion on metal structures of any size before significant degradation has occurred. Evaluation of materials and coatings and the determination or prediction of corrosion performance of both painted and uncoated metal structures or specimens under ambient field or service conditions has traditionally involved visual comparisons which are subjective and require blistering, rusting, or other advanced stages of degradation. The use of laboratory techniques, such as EIS (or AC impedance) has been used to understand and predict corrosion performance during immersion exposures in different electrolytes was limited to small structures or witness specimens that could be immersed, small sections of material cut from large structures, or attachment to the structure of a clamp-on liquid cell in which a liquid or semi-liquid electrolyte and remote counter and reference electrodes were contained.

The immersion of small specimens requires either the destructive sampling of a large structure or the use of witness specimens prepared differently than the actual structure of interest (although the witness specimens and the structure may be prepared at the same time, inherent differences in coating small and large surfaces and inadvertent differences caused by operator error will prevent the witness specimens from being exactly the same as the structure). Additionally, witness specimens will be exposed to slightly different environmental conditions compared to a large structure. Furthermore, the immersion in an electrolyte is not necessarily the exposure condition relevant to the structure being inspected.

Inspection of a large structure using conventional EIS methodologies required complete immersion or use of a clamp-on cell. Such cells would be filled with a liquid or semi-liquid electrolyte (e.g., Kihira el al, U.S. Pat. No. 4,806,849) or a spongy medium impregnated with a liquid electrolyte (e.g., Kondou el al, U.S. Pat. No. 5,221,893) with remote electrodes immersed in the electrolyte or in intimate contact with the electrolyte-impregnated sponge. These cells required an accessible, flat, smooth, and horizontal area. The set-up was considered to be time consuming and had to be performed for each measurement. Corrosion was detected only directly under the cell and use of the cell actually caused artifactual damage to the coating in many instances because of exposure to the electrolyte during measurement.

Davis et al, U.S. Pat. No. 5,859,537, recently developed a painted electrode sensor which eliminates many of the problems discussed above. The actual structure is being inspected without exposure to an extrinsic electrolyte. Measurements are possible under most natural or accelerated conditions and material and coating degradation are detectable from the very early stages. However, the Davis et al, sensor requires an electrode to be permanently painted onto the structure and is time-consuming for all the fabrication steps to be completed. It is not suitable for structures in which appearance or aerodynamics preclude an attached sensor. The sensor can induce artifactual damage in a small class of materials, primarily porous coatings.

Presently, there does not exist a non-invasive corrosion sensing device consisting of an adhesive tape which: (1) provides early detection of both substrate and coating degradation; (2) evaluates substrate or material degradation on structures of any size or composition, under actual conditions, as well as under aggressive corrosive conditions; and (3) can be installed or removed in a expedient and relatively facile manner. Further, no corrosion sensing device currently exists which does not require permanent or fixed attachment to the substrate being evaluated for structural degradation.

SUMMARY OF THE INVENTION

The principal objective of the present invention is to provide a portable and nondestructive adhesive tape which is utilized under actual field or environmental conditions in detecting coating and substrate degradation by electrochemical corrosion of both small and large coated and uncoated metal structures, thereby permitting detection of coating and metal degradation by electrochemical corrosion well before serious deterioration of the material or structure has occurred. The present invention allows for broad applicability, flexibility in utilizing the sensor in various environments without structural compromise and/or the ability to inspect and evaluate corrosion of the actual structure, regardless of the size of the structure. Another distinction between the present invention and the prior art references, with the exception of Davis et al, U.S. Pat. No. 6,054,038, is that the electrodes of the prior art are not readily removed if needed from the sensed substrate. In the present invention, the electrodes may be removed once a measurement is made or remain in the original fixed position so that subsequent measurements may be made with the same electrode.

The foregoing objectives can be accomplished utilizing the present invention as a portable and nondestructive electrochemical device comprised of an adhesive tape sensor for producing an output correlative to an identifiable impedance spectrum (i.e., the impedance magnitude and phase as a function of the frequency of the applied voltage, created utilizing AC Impedance or Electrochemical Impedance Spectroscopy (EIS)).

The preferred embodiment of the invention is as a conductive tape sensor which has a removable and nondestructive sensor apparatus, and provides, as the first element, a pressure-sensitive adhesive tape that comprises a conductive film and conductive adhesive (referred collectively herein as "the conductive adhesive tape"), which when placed in an overlapping configuration with another pressure-sensitive adhesive tape serving as the second element and which comprises a conductive film and non-conductive adhesive (referred collectively herein as "the non-conductive adhesive tape"), produces an electrochemical output correlative to the material to which the conductive and non-conductive adhesives are attached. Both the conductive and non-conductive adhesive tapes may consist of copper foil, but utilization of copper foil as the conductive material of choice is not a requirement. The conductive adhesive tape serves as the sensing element or device. The non-conductive adhesive tape serves as the lead between the sensing element and the point of measurement. Used concurrently with one another through overlapping of the tapes in order to make electrical contact, the conductive adhesive tape serves as a sensor to detect substrate or coating degradation by acting as reference and counter electrodes. In an alternative configuration, the conductive adhesive may be used alone, acting as both sensor electrodes and the lead to the point of measurement. The metal structure or other substrate being sensed or evaluated for degradation serves as the working electrode. Utilizing either configuration, the sensor can be attached to a substrate of arbitrary shape, composition or orientation, with the substrate subject to exposure to selected external agents, physical or chemical, causing electrochemical alterations in the substrate's material; changes in the chemical properties of the materials are then sensed and monitored for changes in the EIS spectra to correlate with the analyzed phenomenon or process for storage, monitoring or control purposes. This two electrode sensing device is responsive to atmospheric, water uptake, incubation, and corrosion, which measures differences in impedance spectra; utilizing, the conductive adhesive tape as both the counter and reference electrodes, applying a small electrical voltage between the substrate, which serves as the working electrode, and the counter/reference electrode and measuring the resulting current based upon the applied voltage between the electrodes. The adhesive tape sensor contemplated in the present invention is pressed against the top coat during inspection, in order to detect varying stages of coating or substrate degradation. Further, the present invention readily detects the early stages of interfacial degradation well before any visual indication of corrosion appears, as well as the ability to detect, quantify and monitor coating and metal degradation from its earliest stages under both laboratory and field conditions.

DETAILED DESCRIPTION OF THE PREFERRED EMBODIMENTS

The invention provides an adhesive in-situ electrochemical tape sensor capable of detecting and monitoring corrosion of an actual structure from its earliest stages of deterioration. This tape sensor utilizes electrochemical impedance spectroscopy (EIS) for investigating corrosion and coating degradation.

Figure 1:
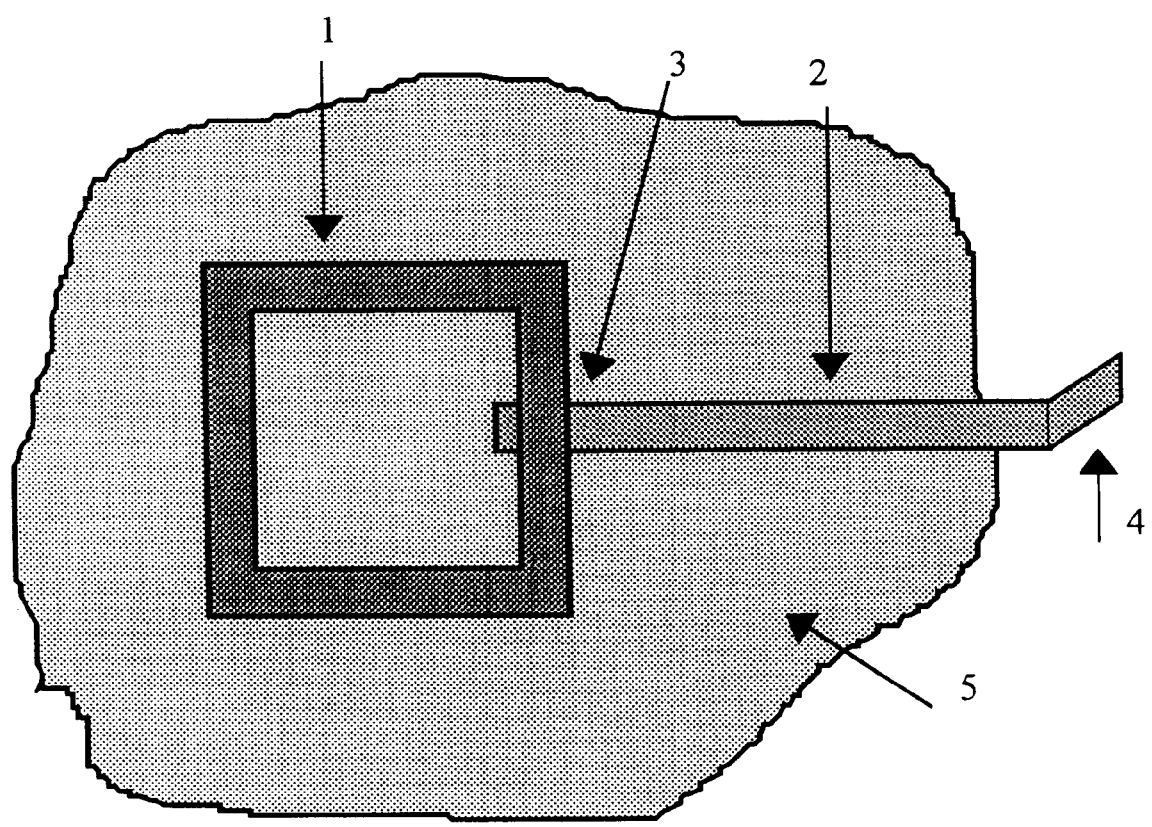
FIG. 1 is a diagrammatic representation of the conductive foil tape with conductive pressure sensitive adhesive. This tape is used to make the sensing element. This open configuration allows the adhesive tape sensor to be permanently mounted for inspection in inaccessible and accessible areas.

FIG. 1 is a diagrammatic representation of the sensing device utilizing conductive foils with conductive pressure sensitive adhesive 1, and non-conductive pressure sensitive adhesive 2 backings. Conductive foil backed with conductive pressure sensitive adhesive is used to make the sensing element. Conductive foil backed with non-conductive pressure sensitive adhesive is used as a lead between the sensing element and the point, measurement. It is necessary for the conductive adhesive sensing element to overlap the non-conductive adhesive lead 4, made by folding the tape back on itself, provides a connection point for measurement devices. The sensor can be attached to a substrate of arbitrary shape and orientation 5.

Figure 2:
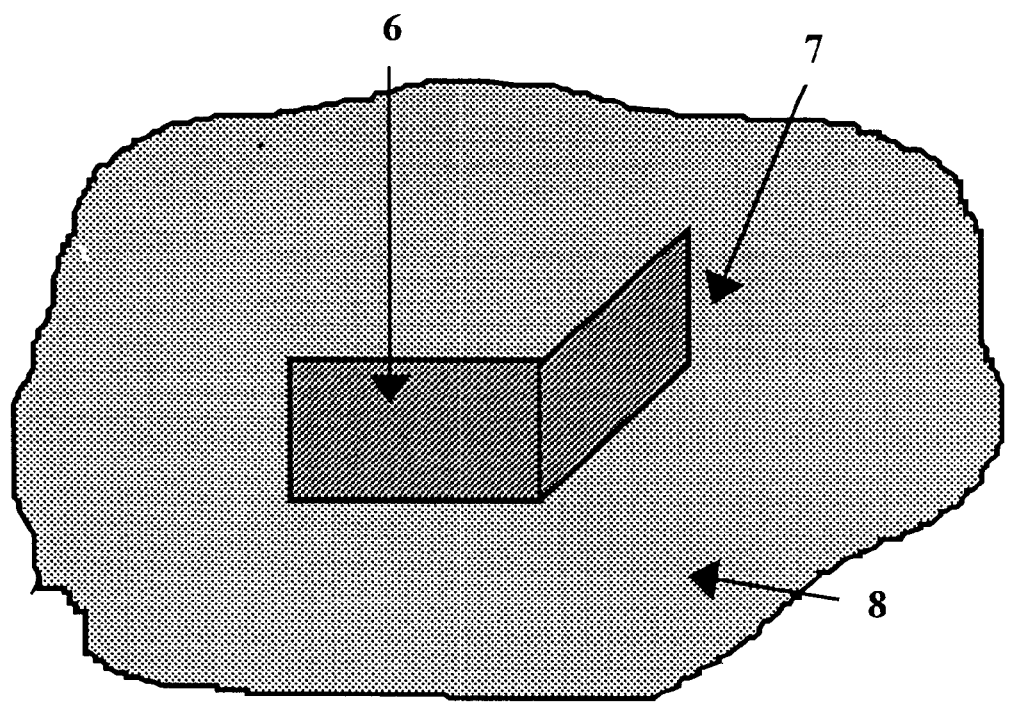
FIG. 2 is a diagram of closed configuration showing the conductive foil tape backed with conductive pressure sensitive adhesive. This sensor is best suited for a one-time measurement in accessible areas.

FIG. 2 is a diagrammatic representation of the sensing device utilizing conductive foil with conductive pressure sensitive adhesive backing 6. Conductive foil backed with conductive pressure sensitive adhesive is used to make the sensing element. A tab at the end of the conductive adhesive lead 7, made by folding the tape back on itself, provides a connection point for measurement devices. The sensor can be attached to a substrate of arbitrary shape and orientation 8. Changes in the chemical properties of the materials are then sensed and monitored for changes in the electrochemical impedance spectroscopy (EIS) spectra to read out information in correlation with the analyzed phenomenon of process for storage, monitoring or control purposes. The adhesive tape sensor produces an output correlative to an identifiable impedance spectrum. An analog signal indicative of the measured current is converted to a corresponding ac impedance signal. A potentiostat with a microcomputer is provided and includes an operational program representative of a functional expression which correlates to distinctive impedance signatures. The impedance spectrum is converted as a function of accelerated exposure and interpreted to determine the stage of corrosion the metal and/or coating has experienced.

We claim:

1. A method for the determination of coating or substrate degradation of a material caused by electrochemical corrosion comprising the steps of:

providing a first adhesive tape element, said first adhesive tape element comprising a first conductive foil and a conductive pressure-sensitive adhesive applied to said first conductive foil;

providing a second adhesive tape element, said second adhesive tape element comprising a second conductive foil and a non-conductive, pressure sensitive adhesive applied to said second conductive foil;

applying said second adhesive tape element to the coating or substrate;

applying said first adhesive tape element to the coating or substrate in a manner that said first and second adhesive tape elements partially overlap each other thereby allowing first adhesive tape element to function as a detection electrode and said second adhesive tape element to function as an electrical lead for said detection electrode;

measuring an electrochemical impedance spectrum between the detection electrode and the material being monitored, said material thereby functioning as a working electrode; and determining the degradation of the coating or substrate from said measured electrochemical impedance spectrum.

2. An apparatus for the determination of coating or substrate degradation of a material caused by electrochemical corrosion, said apparatus comprising:

a first adhesive tape element comprising a first conductive foil and a conductive pressure-sensitive adhesive applied to said first conductive foil;

a second adhesive tape element comprising a second conductive foil and a non-conductive pressure sensitive applied to said second conductive foil;

said first and second adhesive tape elements are arranged on the coating or substrate in a manner that they partially overlap each other with the first adhesive element placed over the second adhesive element allowing the first adhesive tape element to function as a detection electrode and the second adhesive tape element to function as an electrical lead for said detection electrode;

means for measuring an electrochemical impedance spectrum across the detection electrode and the material, said material thereby functioning as the working electrode; and means for determining the coating or substrate degradation based on said measured electrochemical impedance spectrum.

* * * * *